United States Patent [19]
Barrett

[11] Patent Number: 5,728,740
[45] Date of Patent: Mar. 17, 1998

US005728740A

[54] METHOD AND COMPOSITION FOR TREATING BACTERIAL INFECTIONS IN PLANTS

[76] Inventor: Mark William Barrett, 13503 Douglas Dr., Yakima, Wash. 98908

[21] Appl. No.: 761,721

[22] Filed: Dec. 5, 1996

[51] Int. Cl.$^6$ .................. A01N 27/00; A01N 25/02; A01N 25/08; A01N 25/24
[52] U.S. Cl. .................. 514/764; 514/782; 514/783; 424/195.1; 424/196.1; 424/407
[58] Field of Search .................. 514/764, 782, 514/783; 424/195.1, 196.1, 407

[56] References Cited

U.S. PATENT DOCUMENTS

| | | | |
|---|---|---|---|
| 2,128,973 | 9/1938 | Tisdale et al. | 424/658 |
| 2,129,517 | 9/1938 | Goodhue | 514/782 |
| 2,262,454 | 11/1941 | Flenner | 514/782 |
| 2,269,336 | 1/1942 | Davis, Jr. | 424/633 |

OTHER PUBLICATIONS

Lilly Miller brand Pruning Sealer—copy of label and instructions for use. (no date available).

Chevron/Ortho brand Pruning Sealer—copy of label and instructions for use. (no date available).

Pscheidt, Jay "Host: Pear; Disease: Fire Blight," taken from *An Online Guide: 1996 Plant Disease Control*, Botany and Plant Pathology, Oregon State University (pscheidth@bcc.orst.edu). 1996.

Pscheidt, Jay "Host: Pyracantha (Firethorn); Disease: Fire Blight," taken from *An Outline Guide: 1996 Plant Disease Control*, Botany and Plant Pathology, Oregon State University (pscheidth@bcc.orst.edu). 1996.

Pusey, Paul L. "Overview of USDA Fire Blight Program at Wenatchee," USDA—Agricultural Research Service, Wenatchee, Washington. (no date available).

Pusey, Paul L. "Present Distribution of Fire Blight and its Mode of Dissemination—A Review," USDA—Agricultural Research Service, Wenatchee, Washington, 1993.

The Chas. H. Lilly Co. "Health and Safety Information for Lilly/Miller Pruning Aid" MSDSs for xylene and rosin gum. 1995.

Solaris. "Ortho Pruning Sealer MSDS" 1994.

Hercules Chemical Specialties. "Product Data: Hercules FF Wood Rosin," Hercules Incorporated, Resins Division, Hercules Plaza, Wilmington, DE 19894. 1995.

Chemical Abstracts 125:278799 (1996).

Chemical Abstracts 118: 185828 (1992).

Derwent Abstract, Accession No. 97-073204, abstracting JP 08/3199440 (Dec. 1996).

Chemical Abstracts 104: 83788 (1985).

Chemical Abstracts 83: 2296 (1975).

*Primary Examiner*—John Pak
*Attorney, Agent, or Firm*—Stratton Ballew PLLC

[57] ABSTRACT

A method of treating bacterial infection is disclosed. The method comprises the step of applying to a plant having a bacterial infection a composition comprising a xylene source and a wood rosin source, wherein xylene and wood rosin from the xylene source and wood rosin source are present in amounts effective to treat bacterial infection in the plant.

2 Claims, 6 Drawing Sheets

FIG. 6

METHOD AND COMPOSITION FOR TREATING BACTERIAL INFECTIONS IN PLANTS

BACKGROUND OF THE INVENTION

This invention relates to a method and composition for the treatment of bacterial infections in plants and more particularly to a method and composition for the treatment of fire blight in trees.

Most plants are susceptible to bacterial infections such as galls, rots, cankers, wilts, fruit spots, leaf spots, and blights. Pseudomonas, Phytophthora, and *Erwinia amylovora* are some of the bacteria commonly responsible for these diseases.

Of particular concern to apple and pear tree growers is "fire blight", a bacterial infection caused by *Erwinia amylovora*. This prolific bacteria damages susceptible hosts by killing blossoms and twigs and by girdling large branches and trunks. Late in the summer affected trees may look as if they had been scorched by fire, thus the name "fire blight".

The fire blight bacterium proliferates in warm, moist conditions. Moisture may be present in the form of humidity, dew or precipitation; ideal temperatures for fire blight range 60° F. or above. The bacterial source can be a previously infected plant; pruning tools; rain or mist; or an insect or bird carrying the bacteria.

Fire blight infected twigs take on a glassy, water-soaked appearance. They then turn brown or black and rapidly wilt and die. Infected blossoms frequently are distorted. A tan-yellow bacterial exudate often appears at the site of infection.

Cankers can develop on trunks, limbs, and occasionally roots, at first appearing water soaked, then brownish red, and ultimately dark brown or black. Bark covering the cankered area is rougher and separates from the injured tissue. Severe cankers kill or girdle infected limbs.

The fire blight bacteria is extremely virulent. The disease will rapidly spread from limb to limb in a single tree, sometimes making its way into the phloem and xylem of the plant. It will also spread quickly from tree to tree within an orchard.

There are no known apple or pear varieties completely resistant to fire blight, but some are less susceptible than others. In areas where fire blight has become a problem, control of the disease has been attempted by use of antibiotic spray such as streptomycin or teramycin. While such treatment is helpful in preventing the disease, resistant strains of *Erwinia amylovora* are beginning to emerge.

There are two methods currently used to control fire blight. From early in the growing season until the end of blooming, antibiotic or copper sprays can be used to control infection. While these methods are moderately effective, they are also dangerous, expensive, and time consuming. The use of spray chemical requires use of standard spray safety methods, including complete skin and eye coverage, use of a respirator, and at least 24 hour re-entry delay to protect the applicator from adverse affects of the spray. Additionally, sprays are expensive and must be applied every three to five days when ideal fire blight conditions exist. Sprays cannot be used after the end of the blooming period. Finally, sprays are not effective in treating existing fire blight infection; their use is strictly preventative.

There are some disadvantages to the use of copper as a fungicide spray with dormant or delayed dormant or prepink stage. In particular, the products that are used for fire blight (Bordex® or Kocide®) can cause russeting on the fruit, especially when the bud development has exceeded ½" of green tip. Kocide® also is a copper that is mixed with water that is not only being applied to the tree and to the leaves, it is also being applied to the grass and ground, and has a potential to reach groundwater. This disadvantage is also shared by streptomycin and teramycin in applying them in the bloom stage or pink stage. Additionally, the antibiotics may also reach other plant life causing problems. Finally, the antibiotics are also being deposited in the ground during irrigation seasons or heavy rains, and may enter the groundwater posing environmental concerns.

The second fire blight control method is used after infection has occurred. In order to prevent the blight from spreading, the infected limb is excised from the tree six to 18" below the infected site. The limb or limbs removed must be taken out of the orchard and burned to prevent further spreading of the disease. While this method is effective in stopping the spread of fire blight in a tree or orchard, it has obvious drawbacks. The most serious problem with this control method is the loss of fruit producing limbs. In a mature tree, fire blight on a twig may require the removal of 18 inches of a producing limb, which may not seem significant. However, if the infected twig is located near the trunk or a main limb, a substantial part, if not all, of the tree must be removed. In younger trees, almost any fire blight infection results in substantial loss of producing limbs.

Currently, volatile mixtures containing wood rosin and xylene are packaged in aerosol sprays containers as pruning sealers. These aerosol sealing products are widely known in the industry. The aerosol sealers act only as protective paint for application to pruning cuts, grafts, wounds and abrasions on woody plants and trees. The aerosol sealers are employed to provide a durable coating that guards against the entry of moisture, but never as a treatment for bacterial infection. An aerosol formulation of xylene and wood rosin fails to provide the thickness of wood rosin required to adequately arrest the growth of bacteria, namely fire blight as provided by the present invention.

In can be seen from the above discussion that a need exists for a composition and method for treating bacterial infections in plants, without the accompanying environmental concerns and expense.

Furthermore, a need exists for a method of controlling bacterial infections in plants which can be used throughout the growing season.

Additionally, a need exists for a method of controlling bacterial infections in plants which preserves as much of the healthy tree as possible.

A further need exists for a method of controlling bacterial infections in plants which does not rely on antibiotics or chemical sprays.

SUMMARY OF THE INVENTION

The present invention includes a method for treating a bacterial infection in a plant comprising the step of applying to a plant having a bacterial infection an effective amount of a composition including a xylene source and a wood rosin source.

The invention further includes a method for treating a bacterial infection in a plant comprising the step of applying to a plant having a bacterial infection an effective amount of a composition including a xylene source and a wood rosin source, wherein the bacterial infection is fire blight.

The invention also includes a composition for treating a plant bacterial infection comprising a xylene source and a wood rosin source.

Finally, the invention includes a method for preparing a composition for treating a plant with a bacterial infection comprising the steps of: a) liquefying a wood rosin; and b) mixing a xylene source with the liquified wood rosin.

An advantage of the present invention is to provide a method for treating plant cells that are affected by a bacterial infection.

Furthermore, an advantage of the present invention is to provide a method for treating fire blight.

Still another advantage of the present invention is to prevent the loss of an entire tree affected by fire blight.

Moreover, an advantage of the present invention is to provide a method that prevents fire blight from reoccurring at the same infected sight.

Another advantage of the present invention is to provide a method that prevents the spread of a plant bacterial infection.

Another advantage of the present invention is to provide a method that is easy to use.

A further advantage of the present invention is to provide a method for treating bacterial infections in plants that saves on labor costs.

Still a further advantage of the present invention is to provide a method of treating bacterial infections in plants that is safe to the person applying such treatment.

Another advantage of the present invention is to provide a method for treating plant bacterial infections that is more environmentally sound.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method of treating plants having a bacterial infection as well as a method for preparing a composition for use in the method of treating such diseased plants. In an embodiment, a method of treating plants having fire blight is provided comprising the step of applying to a plant having fire blight an effective amount of a composition including a wood rosin source and a xylene source.

In contrast to typical "treatments", the present invention is directed to stopping the spread of bacterial infection without having to destroy the plant infected. To this end, pursuant to the present invention, a composition and a method for applying the composition is provided.

The composition of the present invention is prepared by combining wood rosin and a xylene source. More specifically, FF wood rosin is heated to a temperature of approximately 350° F., or until it becomes a liquid solution. After the solution boils, it is removed from the heat source. Next, xylene is added to the wood rosin solution. Initially, a 25 ml xylene is added per 40 ml rosin. Next, and approximately 1–2 hours after the solution is removed from the heat source, another 25 ml xylene are added to the wood rosin solution to keep it in a liquid form. Finally, an additional 10 ml xylene are added after the solution is completely cooled to keep it in a thin solution.

The wood rosin preferably employed in the present invention is dark wood rosin commonly known as FF wood rosin or gum rosin and has a CAY No. 8050-90-7. The xylene combined with the wood rosin in the present invention can be any mixture of ortho, para and meta forms of xylene, and can also contain ethylbenzene. Preferably a mixture of xylene, CAY No. 1330-20-7 and ethylbenzene, CAY No. 100-41-4 is employed, containing approximately 83% xylene and approximately 17% ethylbenzene, by weight.

Figure 1:
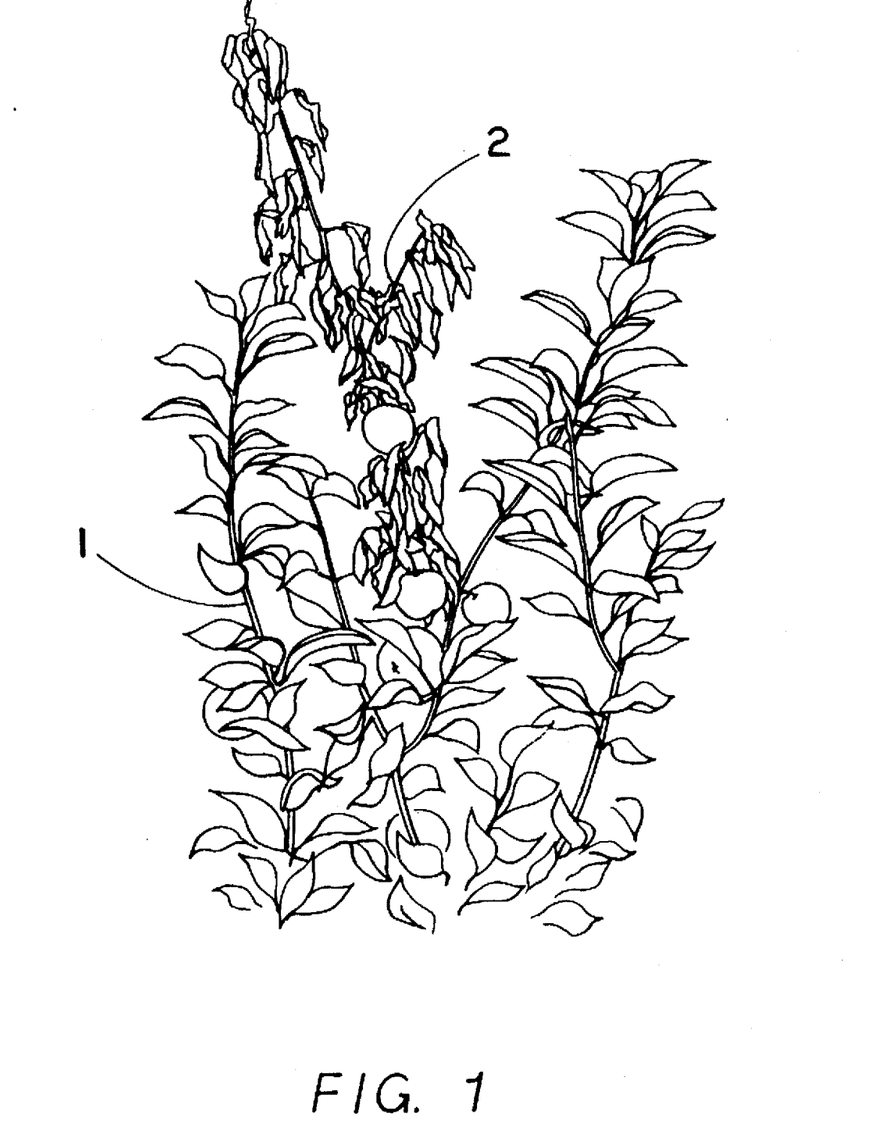
FIG. 1 is a color photograph of an apple tree infected with fire blight.
Figure 2:
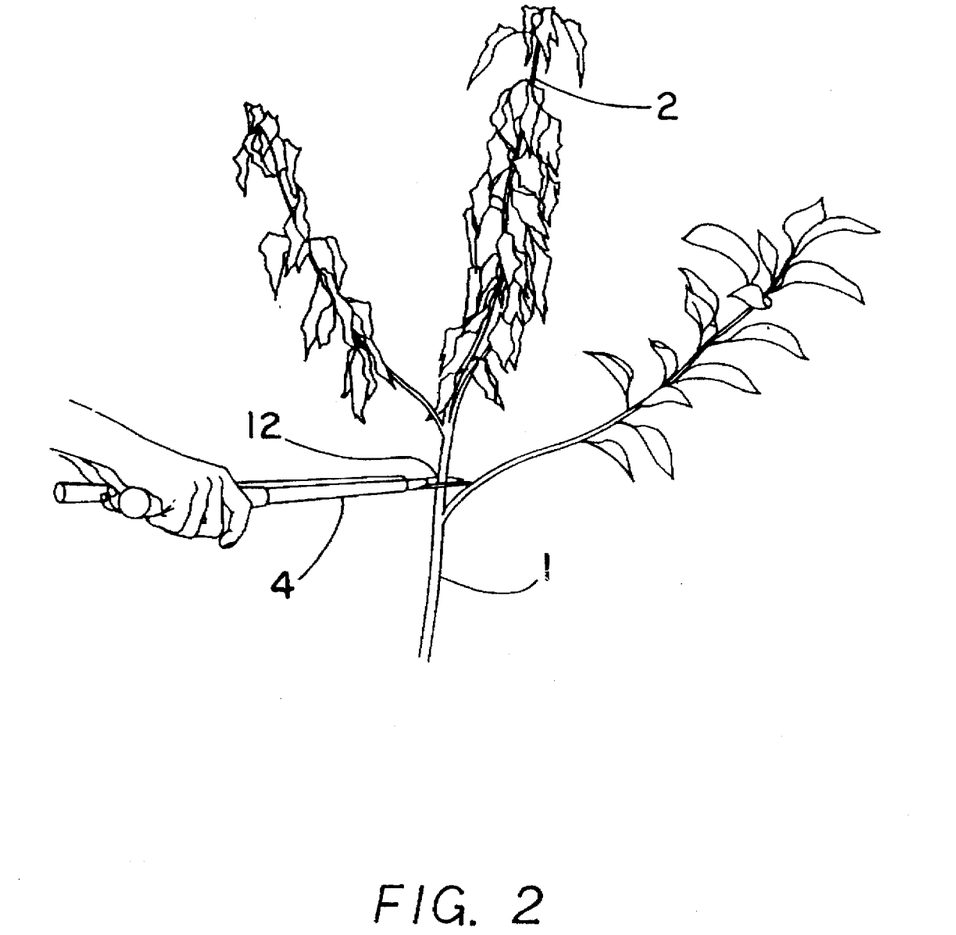
FIG. 2 is a color photograph of a young fruit tree infected with fire blight.
Figure 3:
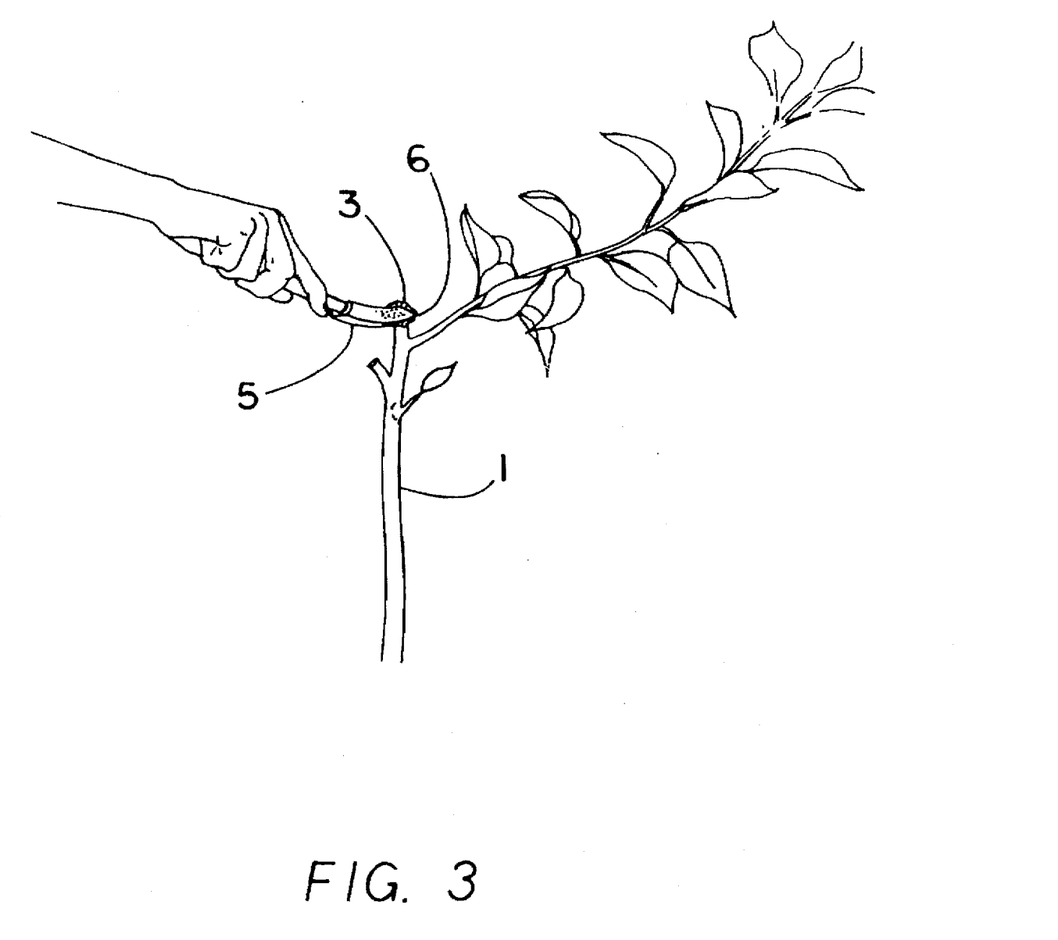
FIG. 3 is a color photograph of the young fruit tree of FIG. 2 being treated with the composition of the present invention, after excision of the infected branch.

In use, the composition of the present invention is administered topically to the infected site, as shown in FIGS. 1–6. First, the blighted area is inspected to determine what is dead and living tissue. FIGS. 1–3 show a young fruit tree 1. The dead tissue 2 is normally the black or browned area or the blighted portion of the limb. Once this determination is made, the dead tissue is excised using a pruner 4, scraper, knife, saw or other appropriate tool, leaving living tissue exposed. The composition 3 is then stirred and applied liberally with a paintbrush 5, dauber or similar device, in a manner that completely covers the affected area 6 to prevent air exposure to the application site. Generally, only one application is required. If the plant exhibits cankers, or if there are blightdarkened limbs, or if the limb that was blighted dripped down onto other tissue, these areas also need to be treated with the composition in order to keep the bacterial cells from propagating. If the infected site is oozing or cankerous, the composition is applied without excising the infected wood. In severe cases, a second application may be needed after one to two weeks. Under extreme conditions, the solution should be applied monthly during the growing season. The solution should be applied to a dry area when the sap is flowing and the ambient temperature is preferably above 32° F. The composition should not be applied to fruit or leaves.

The excised blighted limbs should be removed from the field and burned so that the infected limbs do not infect other parts of the tree from which they were removed, or other trees. Also, sterilizing the pruning tools with a 10% bleach solution or lysol is necessary to avoid spreading the bacteria to other cuts.

Figure 4:
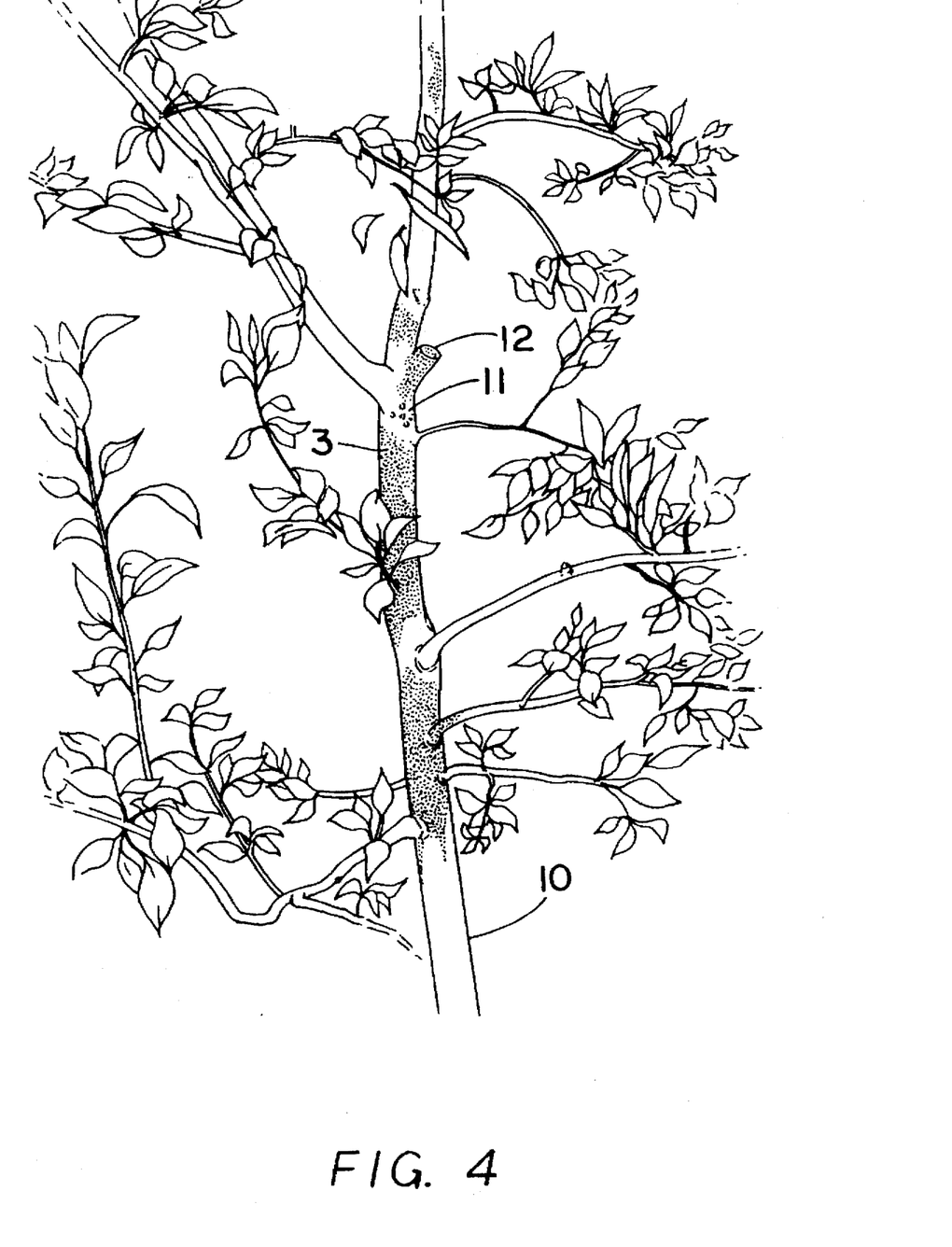
FIG. 4 is a color photograph of a mature fruit tree which has been treated at multiple points along its trunk and limbs with the composition of the present invention.
Figure 5:
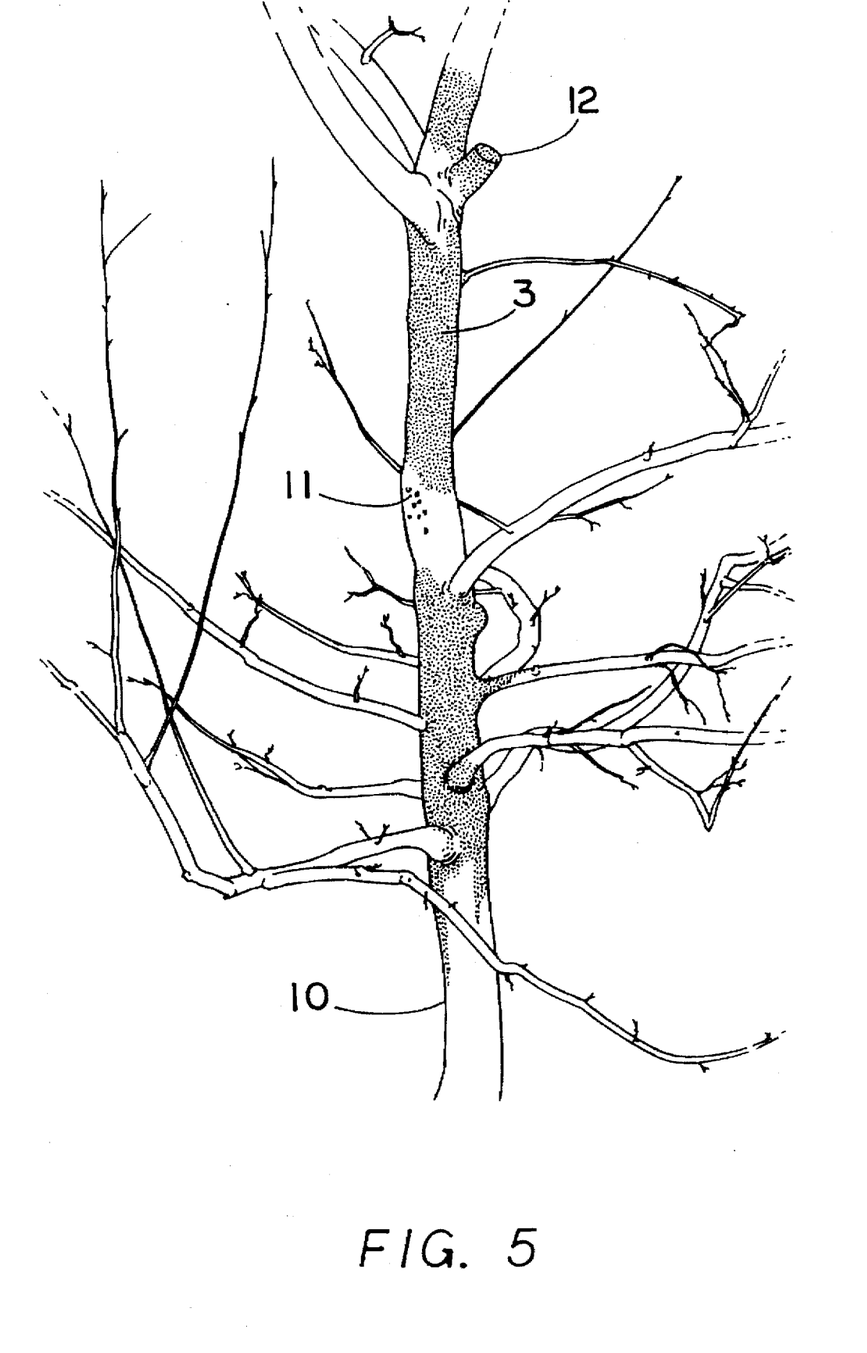
FIG. 5 is a color photograph of the treated mature fruit tree of FIG. 4.
Figure 6:
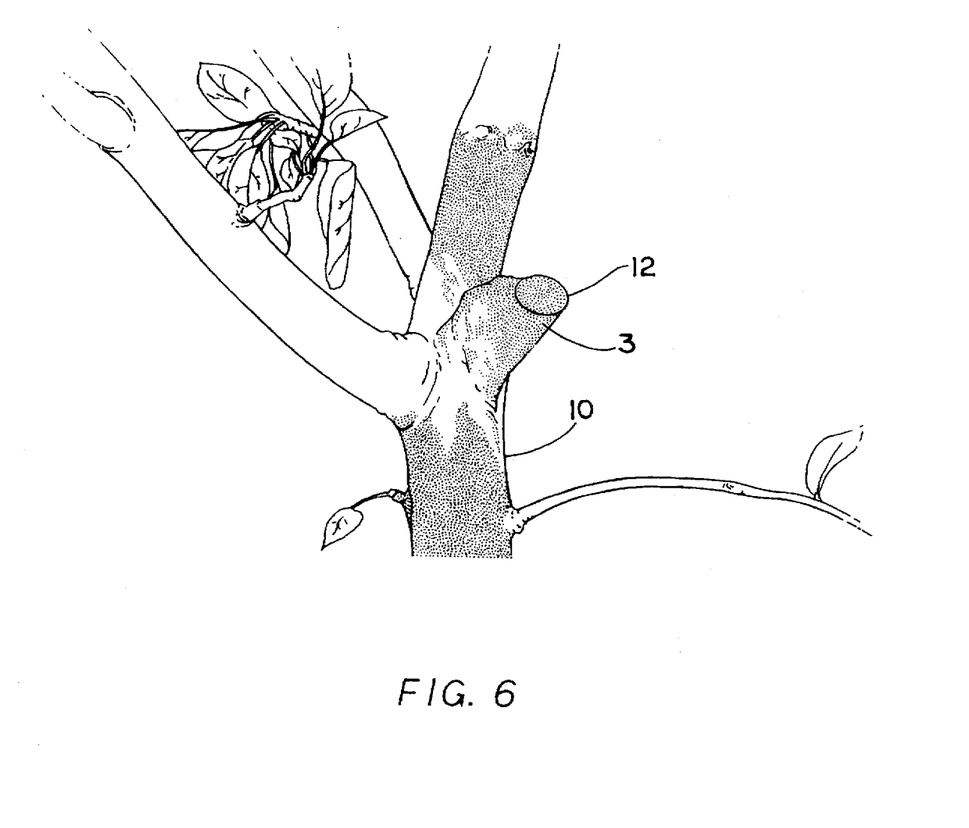
FIG. 6 is a detailed color photograph of the treated mature fruit tree of FIG. 4.

FIGS. 4–6 show a mature fruit tree 10 which has been infected with fire blight. In FIG. 4, the tree is shown in full foliage near the end of the growing season. The composition 3 has been applied to the infected areas 11. FIG. 4 also shows the point of excision 12 of an infected limb. FIG. 5 depicts the same tree during dormancy. FIG. 6 is a close-in view of the point of excision of an infected limb.

It is the inventor's belief that the composition stops bacterial proliferation. Once the composition has been applied to an infected area, fire blight does not return. The composition also seals the infected area from moisture, thereby eliminating the condition necessary for further spread of the infection.

Several field trials were conducted by the inventor. One field trial involved a 5 year old gala apple tree, which was infected on several limbs and on a 24" to 36" length of the central leader. The blighted limbs were excised from the tree and the composition was applied to the excision sites and to the infected central leader. The treated tree was observed for two years, to study how the treatment affected the growth and production of the tree, and to determine whether there was any recurrence of fire blight in the treated areas. No recurrence was evident during the two year observation period. Production was only lost as a result of the excised limb. The normal production of the subject tree was about 4 boxes of fruit; production was reduced by approximately one half box. By comparison, untreated trees in the same block were infected with fire blight so severe that removal of whole trees was required. In the block where I did this test, I removed 10 trees in the first year of the trial.

In another test area, a vigorous 8 year old gala tree was in a block which was severely infected with fire blight. The infected limbs were excised, and the composition applied to the excision site, to open live cankers, and to areas of fire blight discoloration running down the trunk of the tree. The fire blight progression was halted, and no more limbs had to be removed in that block. There were other fire blight strikes on new growth ends, but in contrast to prior years, it was very minimal removal. Labor involved in the control of fire blight was substantially less than it had been in prior years due to the use of the composition.

In another trial, a block severely infected three to four year old Jonagold trees was studied. After the infected tissue was removed and the composition was applied, fire blight did not show up again in that location. By comparison, untreated trees continued to exhibit fire blight infection.

While the above description focuses on the use of the composition to combat fire blight, use of the composition to combat other bacterial, fungal and viral infections is also contemplated by the inventor. Examples of such infections include Phytophthora rot, Algrobacterium, Corynebacterium, Pseudomonas, and Xanthomonas. Also, the composition may be used for treating "replant disease," or on any bark disease that might start a rotting or bacterial infection.

A significant advantage of using the composition of the present invention is that it will save the tree. Without the use of the composition, when fire blight strikes, the limb must be removed. Subsequently, approximately a week or more later, fire blight may return again on the tree necessitating further removal of parts of the tree. It is recommended that the infected limb be excised at a point 6" to 18" below the lowest spot of fire blight. On a five or six year old tree, 18" could easily be half of the tree, and likely includes the major leaders and limbs of production of that tree. If fire blight is found on the main central leader of the tree, the typical treatment is to excise the limb 18" below the infected site. With the composition described herein, only the blighted area need be removed. Therefore, if the tree had an infected 6" twig extending off of its central leader, only the infected twig would need to be excised. The composition would then be applied to the excision site. The composition would then stop the fire blight from striking the rest of the central leader. Instead of whittling the tree away when severe fire blight infections strike, the composition will stop the disease from rapidly progressing. While it is still possible for the fire blight to present itself on other leaders and other limbs, if the composition is applied, it will slow down the possible rapid progression.

Use of the composition results in savings of time and labor. Because the need to inspect and retreat infected trees is reduced, less time is spend in the field.

There are no known chemical treatments which have been proven to be safe and effective during the post bloom stage. This composition can be used at any time before or after bloom, provided the ambient temperature is above approximately 32° F.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principals of the invention, and the disclosure is not intended to limit the invention to the particular embodiments described. Those with ordinary skill in the art will appreciate that other embodiments and variations of the invention are possible which employ the same inventive concepts as described above. Therefore, the invention is not to be limited except by the claims which follow.

What is claimed is:

1. A method for treating a bacterial infection comprising the step of applying to a plant having a bacterial infection an a composition comprising a xylene source and a wood rosin source, wherein xylene and wood rosin from said xylene source and wood rosin source are present in amounts effective to treat bacterial infection in the plant.

2. The method of claim 1 wherein the bacterial infection is fire blight.

* * * * *

UNITED STATES PATENT AND TRADEMARK OFFICE
CERTIFICATE OF CORRECTION

PATENT NO. : 5,728,740
DATED : March 17, 1998
INVENTOR(S) : Mark William Barrett It is certified that error appears in the above-indentified patent and that said Letters Patent is hereby corrected as shown below:

Col. 3, line 36, change "color photograph" to --diagram in perspective--;
3, line 38, change "color photograph" to --diagram in perspective--;
3, line 40, change "color photograph" to --diagram in perspective--;
3, line 43, change "color photograph" to --diagram in perspective--;
3, line 46, change "color photograph" to --diagram in perspective--; and
3, line 48, change "color photograph" to --diagram in perspective--.

Signed and Sealed this

Twenty-eighth Day of July, 1998

*Attest:*

BRUCE LEHMAN

*Attesting Officer*        *Commissioner of Patents and Trademarks*